United States Patent [19]
Hsei et al.

[11] Patent Number: 6,159,160
[45] Date of Patent: Dec. 12, 2000

[54] SYSTEM AND METHOD FOR CONTROLLED INFUSION AND PRESSURE MONITORING

[75] Inventors: Paul K. Hsei, San Jose; Christopher R. Clare, Los Altos Hills; Donald L. Alden, Sunnyvale, all of Calif.

[73] Assignee: Ethicon, Inc., Somerville, N.J.

[21] Appl. No.: 09/146,798

[22] Filed: Sep. 3, 1998

Related U.S. Application Data

[60] Provisional application No. 60/079,515, Mar. 26, 1998.

[51] Int. Cl.$^7$ ...................................................... A61D 5/00
[52] U.S. Cl. ............................................................ 600/560
[58] Field of Search ...................................... 600/573, 578, 600/579, 560; 604/67, 49, 317, 322

[56] References Cited

U.S. PATENT DOCUMENTS

| | | |
|---|---|---|
| 4,449,538 | 5/1984 | Corbitt et al. . |
| 4,838,856 | 6/1989 | Mulreny et al. . |
| 4,995,268 | 2/1991 | Ash et al. . |
| 4,998,714 | 3/1991 | Wiest et al. ................................ 604/67 |
| 4,998,914 | 3/1991 | Wiest et al. . |
| 5,489,265 | 2/1996 | Montalvo et al. . |
| 5,492,529 | 2/1996 | Neuwirth et al. .......................... 604/47 |
| 5,492,537 | 2/1996 | Vancaillie . |

OTHER PUBLICATIONS

Willem M. Ankum, Jan Vonk, "The spring balance: a simple monitoring system for fluid overload during hysteroscopic surgery," The Lancet, vol. 343, Apr. 2, 1994, pp 836–837.

G.J. Shirk, R.J. Gimpelson, "Control of Intrauterine Fluid Pressure During Operative Hysteroscopy," J. of Am. Assn. of Byn. Lap., vol. I, May 1994, pp 229–233.

Paulette Stafford, "New Technology Helps Prevent Fluid Intravasation During Operative Hysteroscopy," Minimally Invasive Surgical Nursing, vol. 11, No. 2, 1997, pp. 63–66.

*Primary Examiner*—Cary O'Connor
*Assistant Examiner*—Pamela Wingood
*Attorney, Agent, or Firm*—Verne E. Kreger, Jr.

[57] ABSTRACT

Improved systems and methods are used for controlled infusion of fluid into a body cavity. In particular, the improved system allows a user to accurately control pressure created in a body cavity over a broad range of fluid flow rates required in various medical procedures. In one embodiment, the system comprises a pump having a conduit which defines a fluid flow path from the pump. Typically, a surgical instrument such as a resectoscope is coupled to the conduit to direct the fluid into the body cavity. The system controls pressure in the body cavity by using a first sensor to measure pump output and a second sensor to measure body cavity pressure. Preferably, the second sensor measures the actual pressure in the body cavity to correct for any pressure losses that may occur during fluid delivery from the pump.

33 Claims, 8 Drawing Sheets

FIG. 9

SYSTEM AND METHOD FOR CONTROLLED INFUSION AND PRESSURE MONITORING

CROSS REFERENCE TO RELATED APPLICATIONS

The present application is related to and claims priority from U.S. Provisional Patent Application Ser. No. 60/079,515 entitled "System and Method for Controlled Infusion and Pressure Monitoring" filed on Mar. 26, 1998, the full disclosure of which is incorporated herein by reference for all purposes.

BACKGROUND OF THE INVENTION

The present invention is related to medical devices, and more particularly to medical devices for controlled infusion of fluid into a patient during a medical procedure.

Controlled fluid infusion is crucial in many medical procedures. In some procedures, fluid is used as a distending medium, inflating a body cavity to provide space for surgical instruments and to gain access to a target site in the body cavity. In other procedures, fluid infusion is used to flush out impurities or tissue debris from the patient which may impair visualization and operating efficiency. During the course of such procedures, large volumes of distention fluid such as saline may be circulated in and out of the patient. Unfortunately, poorly controlled infusion of such volumes of fluid can create electrolyte imbalance, water intoxication, or excessive fluid pressures that may be dangerous or even fatal to the patient.

The danger posed by inaccurate fluid infusion, specifically poor fluid pressure control, is particularly relevant to many endoscopic procedures. As an example, hysteroscopic endometrial resection and transurethral resection procedures circulate fluid in and out of the uterus and the bladder, respectively, to provide distension and to remove debris. These body cavities are, however, pressure sensitive environments. Introducing too much fluid too quickly could push distention fluid into the circulatory system of the patient, or worse, rupture these body cavities and cause major internal trauma. Insufficient fluid flow, on the other hand, could cause the body cavity to collapse, reducing the amount of space available for surgery and impairing visibility of the active end of any surgical instruments in the cavity. Hence it is desirable that a user or surgeon be able to accurately control fluid infusion so that the pressure within a body cavity is near an optimal level.

Conventionally, fluid has been infused into a patient by hanging a fluid bag or bottle above the patient and relying on gravity to infuse fluid into the patient. Common practice today eliminates the reliance solely on gravity by using fluid pumps to infuse fluid into the body cavity through a fluid inlet and/or to suction fluid out through a fluid outlet.

Unfortunately, these conventional infusion systems are unable to adequately regulate fluid pressure in a body cavity when there is dynamic fluid flow. Conventional systems typically have pressure controllers that only measure pressure outside of the body cavity, typically using only a single pressure sensor. Although such conventional systems may be able to control body cavity pressure when the fluid is static, once fluid flow starts, the actual pressure inside the cavity may be significantly different from pressure measurements made outside the cavity. Dynamic fluid flow exacerbates pressure drops and measurement errors which occur along the fluid flow path from the fluid source to the point of delivery. Even pressure measurements made closer to the body cavity along the fluid flow path are inaccurate since much of the pressure drop occurs in the instrument or surgical tool delivering fluid into the body cavity. Such discrepancies in pressure may be in the range of 20 to 30 mm Hg and is a significant cause for concern, especially in a rupturable, pressure sensitive environment such as the uterus or the bladder.

Accordingly, it is desirable to have improved fluid infusion methods and systems which are highly accurate, can achieve a desired-fluid pressure in a body cavity, and are stable and responsive. In particular, such a system should overcome the dynamic instability problems associated with prior pump systems to deliver fluid through endoscopic and other instruments into the body cavity, while retaining responsive closed loop control. It would further be desirable if these improved systems were adaptable for use with known endoscopic and other minimally invasive surgical techniques.

SUMMARY OF THE INVENTION

The present invention provides improved systems and methods for controlled infusion of fluid into a body cavity. In particular, the present invention provides a system that is both stable and sufficiently responsive during dynamic flow of fluid through the system. This reduces the likelihood of pressure oscillations that may cause damage to internal organs or excessive fluid absorption by a patient. Advantageously, the system of the present invention also allows a user to accurately control pressure created in a body cavity over a broad range of fluid flow rates used in various medical procedures.

In analyzing the problem, inventors have noted that the relatively slow response time of most fluid delivery systems complicates the control of fluid infusion. In practice, because of the slow response, a system using a single pressure sensor is either highly unstable or impractically slow. This is because it takes a substantial amount of time for changes in pump output to reach the environment inside the body cavity. Oscillations result from this lag because the effects in the body cavity of increasing or decreasing pump output at pump are not registered in time by the sensor. The sensor is constantly overcorrecting or undercorrecting the pump driving pressure to compensate for conditions in the body cavity. Such oscillations are highly undesirable as extreme pressure changes may result, causing the body cavity to burst or forcing distention fluid into the circulatory system. Attempts by known systems to reduce such oscillatory behavior typically result in a very slow responding system which damps out overshoot and undershoot associated with the control loop.

The controlled infusion system of the present invention generally comprises a pump connectable to a fluid source and a conduit having a proximal end and a distal end. The distal end of the conduit is connectable to an infusion instrument that preferably delivers fluid into a body cavity. For surgical procedures in the uterus, the infusion instrument is typically a resectoscope. In one embodiment, the present system has a first sensor disposed to measure pump output and a second sensor adapted to measure body cavity pressure. The measured pump output and measured body cavity pressure are used by a controller to control pump output. The controller has a control loop which generates the pump output set point based on a body cavity pressure set point and the measured body cavity pressure. This pump output set point along with the measured pump output is used by another control loop to control pump output.

By using a system that obtains pressure information from at least two points or locations, a preferred embodiment of the present invention addresses many of the stability and responsiveness issues plaguing conventional infusion systems. For example, the pump controller preferably controls pump speed based on pressure within the body cavity and also pressure of pump output. In one particular embodiment, a first sensor measures pump output pressure immediately downstream from the pump. The control loop of this embodiment formed by the sensor, the controller, and the pump is a relatively short loop, and this provides for responsive yet stable control of the pump speed creating pump driving pressure. In this first loop, the lag between changes in pump output and detection by the first sensor is relatively small. To improve the accuracy of the first loop, in terms of actual pressure in the body cavity, a second control loop in this embodiment formed by a second sensor, the controller, and the pump adds a correction factor to the first loop. The second sensor, which preferably measures pressure within the body cavity, is used to define the correction factor added to the first control loop. The correction factor increases or decreases the pump offset in the first loop so that the driving pressure of the pump compensates for all pressure losses that occur prior to delivery of fluid into the body cavity.

In preferred embodiments, the second sensor of the infusion system is fluidly or pneumatically coupled to a sensing tube which is coupled to the resectoscope. The sensing tube has a static pressure port which is preferably located within the body cavity when the device is in operation. This brings pressure information to the second sensor. In preferred embodiments, the system also includes a bubble trap coupled to the fluid conduit. The bubble trap preferably acts as a liquid flow smoothing device for the system to reduce undesirable pulsatile flow from the pump. In addition to the smoothing function, the bubble trap accumulates undesirable air flowing through the fluid lines.

In another aspect, the present invention provides a device for use in a body cavity comprising a resectoscope having pressure sensor coupled to a sensing tube in the sheath of the resectoscope. Preferably, the sensing tube has a static pressure port fluidly coupled to the body cavity. The use of a sensing tube allows the pressure sensor to avoid direct contact with the operating environment of the device. Advantageously, coupling the sensor to the sensing tube, aside from reducing wear on the sensor, also facilitates removal of the sensor for repair or replacement. The resectoscope is typically fluidly coupled to a fluid source and may have a cutting device located near the distal end of the sheath.

In another aspect, the present invention provides a method for irrigating a body cavity. In one embodiment, the method comprises pumping a fluid to the body cavity using a controllable pump. The method measures pressure in the body cavity and the pump output over time. The pressure in the body cavity is controlled by determining a pump output factor based on the measured body cavity pressure and controlling the pump output based on the pump output factor and the measured pump output. The pump output factor may comprise the pump output pressure or a correction factor to the pump output pressure.

In another embodiment, the method of the present invention involves controlling pump speed based on a correction factor and fluid pressure near the pump, where the correction factor is usually calculated based on the pressure in the body cavity. The method comprises using a pump to flow fluid through a fluid conduit into the body cavity. The correction factor is based on a fluid pressure near a target site in the body cavity. Pump output is controlled by adjusting pump speed based on the correction factor and fluid pressure near the pump. The method preferably measures pressure from at least two locations along the fluid delivery pathway. Alternatively, the method may involve controlling the power applied to the pump (instead of the pump speed) to control pump driving pressure. The pump may also be a fixed output pump that has an adjustable or variable output bypass.

A further understanding of the nature and advantages of the invention may be realized by reference to the remaining portions of the specification and the drawings.

DETAILED DESCRIPTION OF THE SPECIFIC EMBODIMENTS

The systems and methods of the present invention will significantly facilitate the accurate control of fluid pressure within a body cavity during the dynamic flow of fluid circulating through the cavity during a medical procedure. These methods and systems are particularly well adapted for minimally invasive endoscopic procedures requiring controlled infusion of fluid into a body cavity, such as for hysteroscopic endometrial resection, transurethral resection, and various laparoscopic or arthroscopic procedures performed inside a patient. The fluids infused into the patient are preferably physiological liquids, such as sterile saline solutions, but it may also be non-physiological solutions such as glycine, methanol, etc. The use of liquids are usually preferred since they reduce the risk of embolic complications. Controlled infusion into the body cavity is generally used to maintain manual access and optical visualization of a surgical target site in the body cavity. Preferably, by positioning an endoscope, laparoscope, or the like within the body cavity to provide a fluid flow pathway, the body cavity will remain distended and clear of tissue debris, allowing generally uninterrupted surgery at the target site. While it is understood that the present invention may be used in a variety of medical procedures, for ease of illustration, the remainder of the specification will describe the present invention in the context of a uterine resection procedure.

The present invention is of particular use in controlled fluid infusion. As used herein, the term "controlled infusion"

is used broadly to include any type of pressurized fluid flow whether it be for irrigation or for other purposes such as debris removal or body cavity distention. The present invention may also use a plurality of pressure sensors. The term "sensor" as used herein includes those devices which directly sense pressure and also those devices which use a transducer and some type of connector, such as an air conduit or electrical wire, to bring pressure information back to a pressure measuring element. The present invention may also include some type of fluid pump. The term "driving" or "output" pressure as used herein refers to the fluid pressure at points near and preferably downstream from the pump. These terms describe the pressure associated with fluid flowing from the pump which have not experienced significant pressure losses due to fluid dynamics. The driving or output pressure usually does not equal actual body cavity pressure when fluid is flowing.

Figure 1:
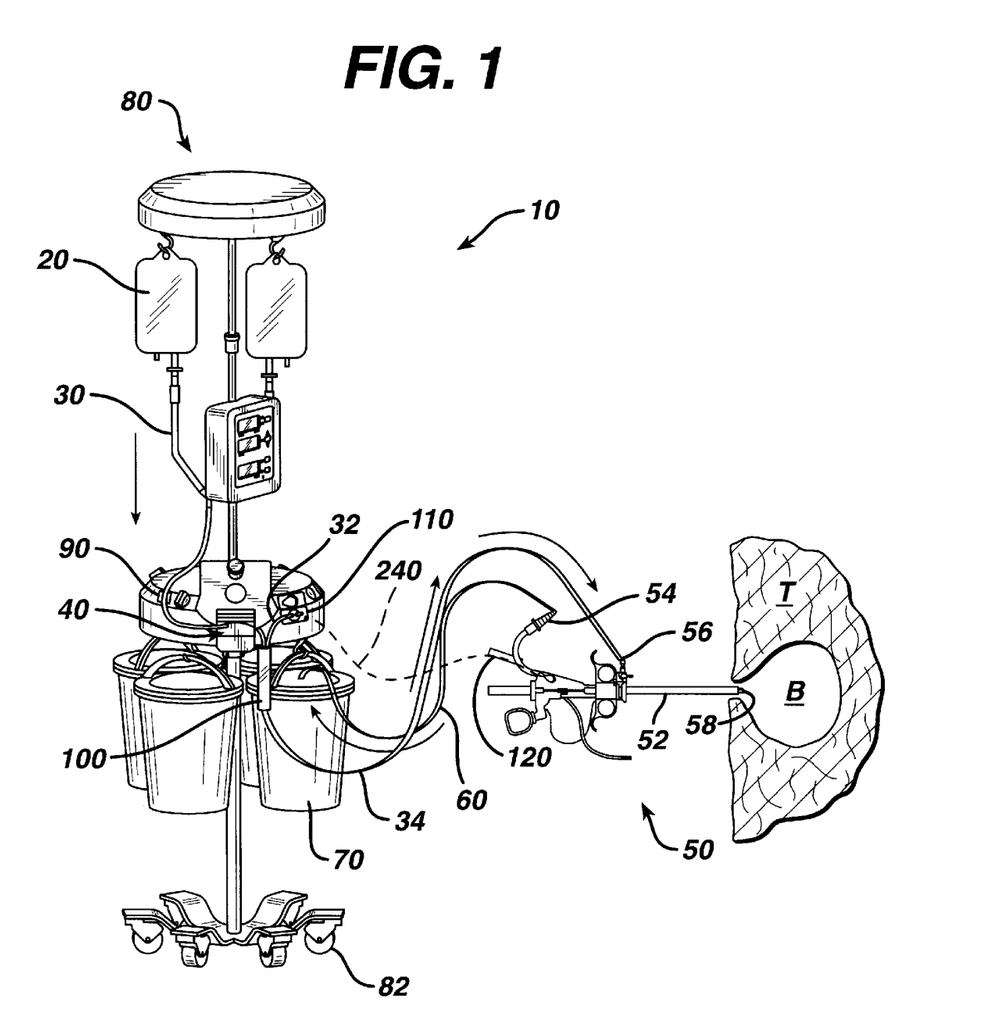
FIG. 1 is a perspective view of a preferred embodiment of a system according to the present invention.

Referring now to FIG. 1, a controlled infusion system 10, according to the principles of the present invention, will be described in detail. The embodiment of the controlled infusion system 10 illustrated in FIG. 1 is configured for uterine resection. The system 10 includes at least one fluid source 20, coupled by a fluid conduit 30, to a pump 40, which is preferably a positive displacement device such as a peristaltic pump, to prevent the backflow of used irrigation fluid into the fluid source 20. Fluid output from pump 40 travels through conduit 34 to an infusion instrument such as a resectoscope 50. Conduit 34 may be a continuous piece of tubing with conduit 30 or a separate piece of tubing or material. The fluid is then circulated into a body cavity B through resectoscope sheath 52 and out through tube 58. Although the sheath 52 is preferably removably coupled to the resectoscope 50, the sheath 52 may also be permanently connected to the device. The circulated fluid provides distension to visualize the target site T in the body cavity and to remove tissue debris. The fluid flow rate may be as high as about 1.0 liters/min, more preferably in the range between about 0.4 to 0.8 liters/min. Of course, higher flow rates may be used to withdraw the tissue debris and other material through the resectoscope. Circulated fluid exits the resectoscope 50 through resectoscope outflow 54 fluidly coupled to outflow line 60 which empties out to waste container 70 for collection and removal. A suction pump may be coupled to the waste container 70 to facilitate the withdrawal of fluid and to adjust the fluid flow rate through the system 10.

To minimize space consumption in an already crowded operating room environment, preferred embodiments of the infusion system 10 include a mounting chassis 80 on which the fluid sources 20, pump 40, and waste container 70 can be mounted. The chassis 80 typically incorporates a plurality of castor wheels 82 to facilitate the positioning of the chassis 80 near the patient during the medical procedure. Preferably, the pump 40 is located at about the same height as the patient, about 3 to 4 feet above the ground.

Figure 2:
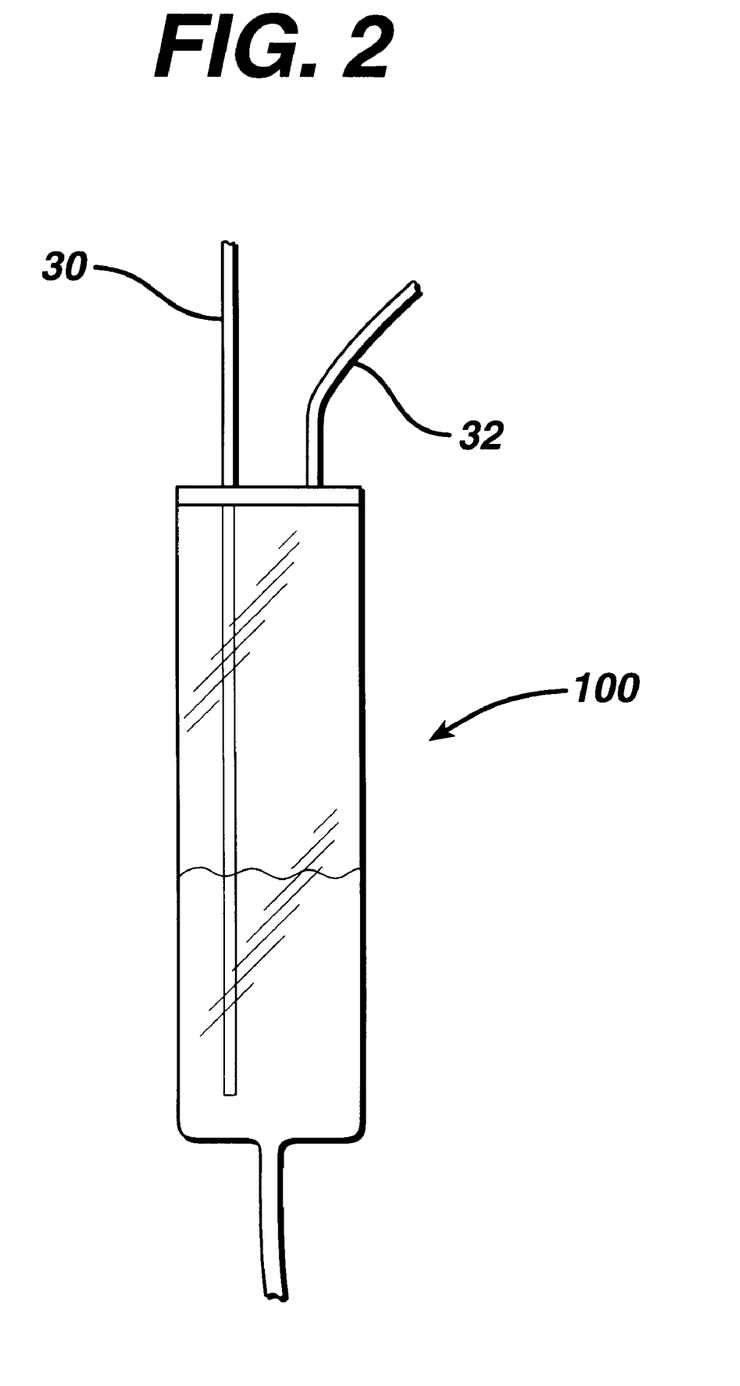
FIG. 2 shows a preferred embodiment of a bubble trap for use with the system of FIG. 1.

Referring now to FIGS. 1 and 2, a bubble detector 90 and a bubble trap 100 are located along the fluid flow path prior to delivery of the physiological fluid into the resectoscope 50. The presence of air bubbles in the infused fluid is undesirable as open blood vessels in the uterus and near the fimbriae of the ovaries increase the risk of air embolisms in the circulatory system of the patient. Detection of air by the sensor 90 will preferably result in some form of audible or visual signal to notify the user of the air bubbles and preferably stop the pump. As more clearly illustrated in FIG. 2, bubble trap 100 will typically prevent the passage of any air bubbles into the resectoscope 50.

In preferred embodiments, the bubble trap 100 is made of a clear, inert material such as glass or certain polymers which allow for visual observation of the infusion process but do not react chemically with the physiological fluid. The bubble trap 100, although not limited in this manner, preferably contains enough fluid or liquid to cover the tip of conduit 30 while being at least partially and more preferably about ½ filled with fluid. This air filled empty space, as discussed in detail below, provides a damping quality which smooths any pulsatile flow coming from the driving pump, particularly a peristaltic-type pump. Sensor line 32 of the first pressure sensor 110 is also typically coupled to the top of the bubble trap 100. The bubble trap is usually located just downstream from pump 40 so that the first sensor 110 senses the drive pressure from the pump. It is understood, however, that sensor 110 may be fluidly coupled directly to the conduit 34 or pump 40 without passing through the bubble trap 100. Preferably, first pressure sensor 110 is of a diaphragm configuration, as known in the art, which creates a separation between the sensor 110 and the fluid being sensed.

Referring again to FIG. 1, the controlled infusion system 10 of the present invention preferably contains at least two pressure sensors 110 and 120. These two sensors 110 and 120 measure fluid pressure at two different, spaced-apart locations along the fluid flow path. In preferred embodiments, the sensor 110 measures pressure immediately downstream from the pump while sensor 120 measures the fluid pressure inside a body cavity B. In an alternative embodiment, the sensor 120 may be coupled by a connector, such as a Y or T connector, to the resector inflow 56 to sense dynamic pressure of fluid just before the fluid enters the resectoscope. Although still improving pressure control to some degree, the positioning of the sensor 120 to measure pressure just outside the infusion instrument is still noticeably less accurate than configurations of the system 10 where sensor 120 senses the actual pressure inside body cavity B.

Figure 3:
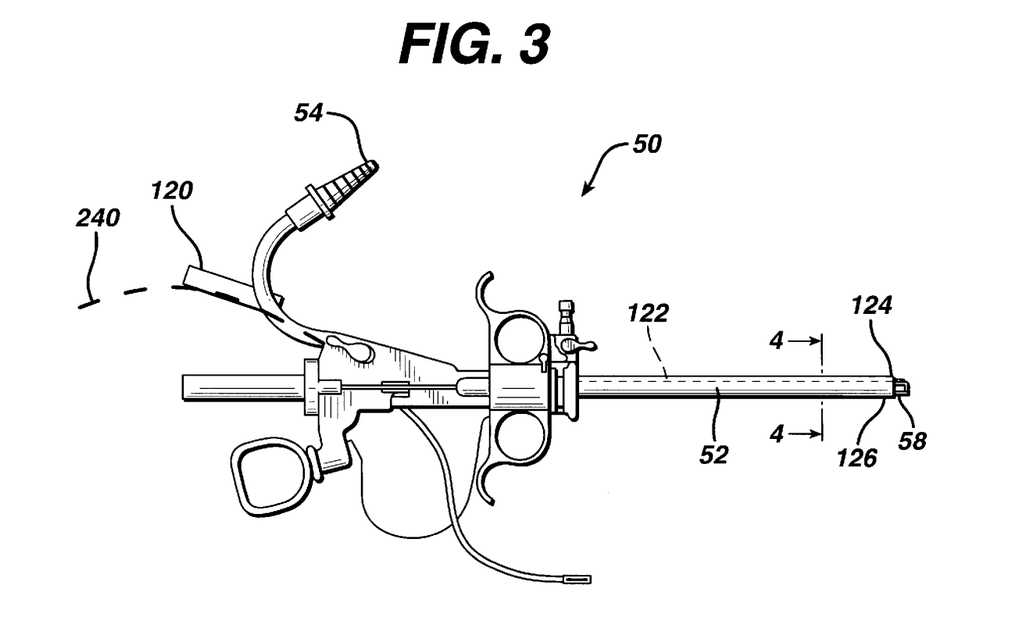
FIG. 3 is a side view of a resectoscope for use with the system of FIG. 1.
Figure 4:
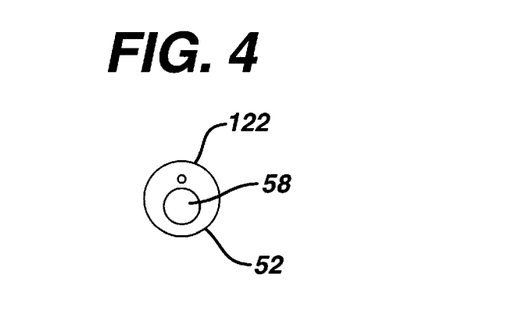
FIG. 4 is a cross-sectional view of the sheath of the resectoscope of FIG. 3.
Figure 5:
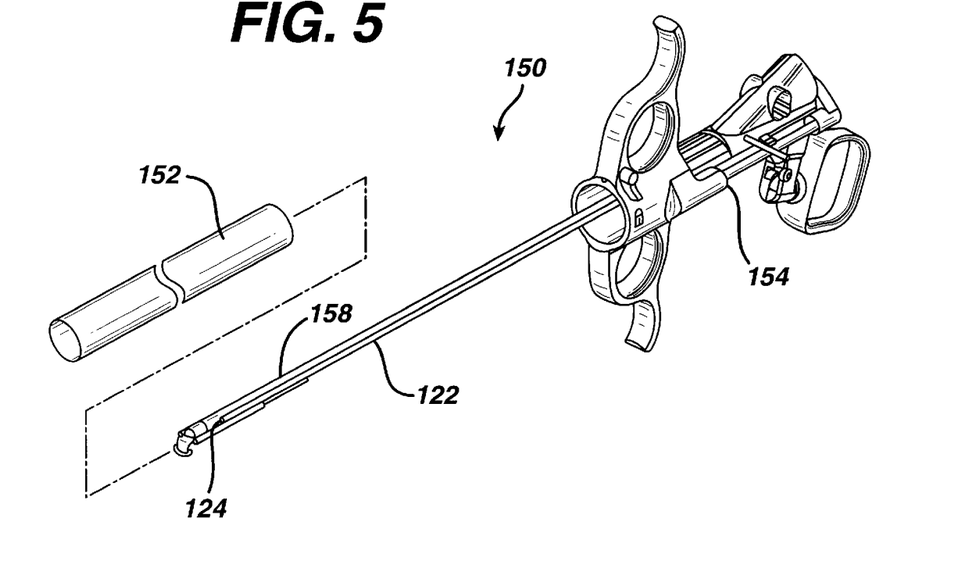
FIG. 5 is a perspective view of an exemplary embodiment of a resectoscope for use with the system of FIG. 1.
Figure 6:
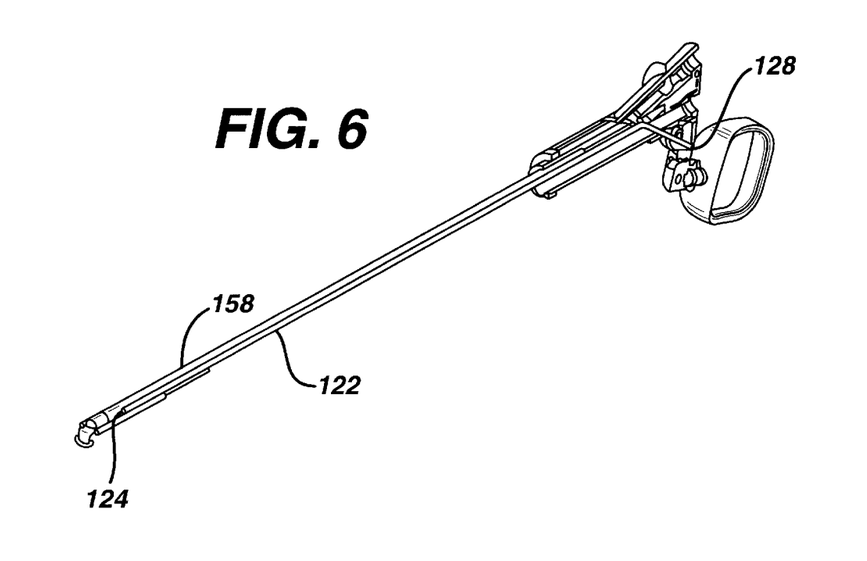
FIG. 6 is a partial cut-away view of the resectoscope of FIG. 5.

Referring now to FIGS. 3 and 4, a preferred embodiment of the resectoscope 50 is shown having sensor 120 mounted on the proximal end of the resectoscope 50. A sensing tube 122 is coupled to the sensor 120 and has a static pressure port 124 preferably located near the distal tip 126 of the resectoscope sheath 52. The sensing tube 122 communicates pressure from the body cavity B to the second pressure sensor 120, which is located outside the body cavity. As shown in FIG. 4, the sensing tube 122 may be positioned within the resectoscope sheath 52 or more preferably may be located on the exterior of sheath 52 as shown in FIGS. 5 and 6. Although a variety of different sizes may used, the outer diameter of the sensing tube 122 is typically about 0.03 to 0.08 inches in diameter. The sensing tube 122 is sized to minimize interference with the operation of the resectoscope 50. The sheath 52, including sensing tube 122 and other tubes for inflow/outflow, preferably has sufficient size to allow the withdrawal of tissue chips created during uterine resection. The sensing tube 122 is also sized to reduce the likelihood of fluid entering into tube 122 through static port 124.

The static port 124 may be located in a variety of positions along the resectoscope sheath 52, so long as the static port 124 is capable of sensing pressure in the body cavity B when the resectoscope is in use. For example, FIGS. 5 and 6 show an exemplary embodiment of the resectoscope 150 where the sheath 152 has been removed, exposing the sensing tube 122 which is located adjacent tube 158. It should be understood, however, that the tube 122 may also be located in a variety of positions outside the sheath 152, such as on the surface of the sheath 152, as an alternative embodiment. As shown in FIG. 6, the proximal end of sensing tube 122 protrudes from the handle portion 154 of the resectoscope 150, to facilitate the connection of second sensor 120.

The resectoscope 150 typically has a suitable cutting device near the distal end 126 to cut and remove tissue from a surgical target site T. Details of a suitable cutting device such as a morcellator or RF ablation tool may be found in commonly assigned, co-pending U.S. patent application Ser. No. 08/906,358, filed Aug. 5, 1997 (Attorney Docket No. 16944-002400), the complete disclosure of which is incorporated herein by reference. The materials used for the cutting device and the resectoscope are preferably resistant to cleaning by normal medical disinfectant solutions, such as alcohol or glutaraldehyde, and with standard gamma sterilization processes.

Figure 7A:
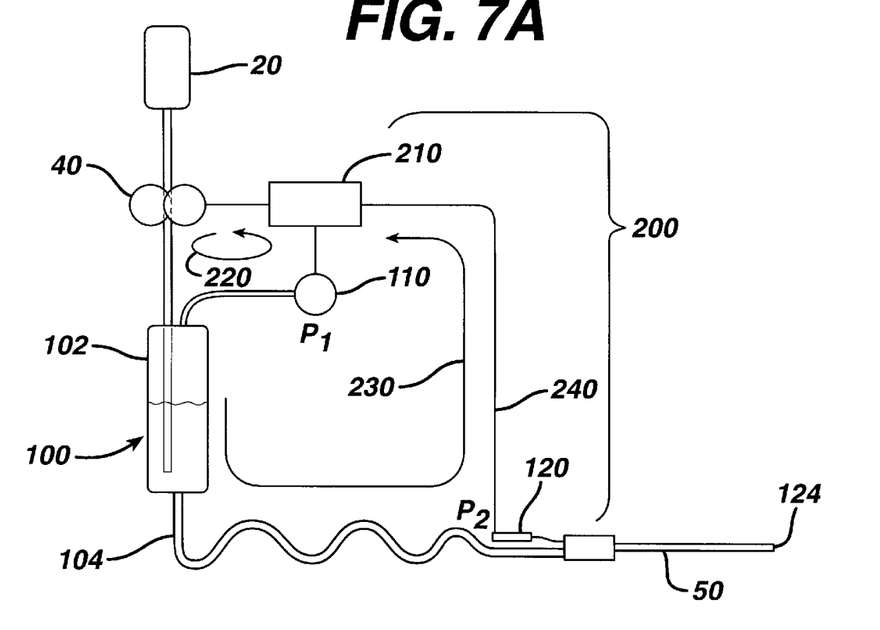
FIG. 7A is a schematic of a preferred embodiment of the system of according to the present invention.

The second pressure sensor 120 is preferably located outside of the patient when the resectoscope is in operation. It is coupled by a connector, such as a wire 240, to pump controller 210 (FIG. 7A). Advantageously, locating the sensor 120 near the proximal end of the resectoscope reduces the exposure of the sensor to the operating conditions inside the body cavity B. It also allows the controlled infusion system 10 to be adapted for use with conventional resectoscope designs. As seen in FIG. 3, the sensor 120 is preferably located at the same horizontal level as the location of the static port 124. This reduces any errors or discrepancies in pressure due to height of fluid in the sensing tube 122 since the sensor 120 and the static port 124 are at the same level. Alternatively, the sensor 120 may be positioned back on the pump 40 and be coupled to the distal end 124 of the sensing tube 122 by an air conduit (not shown). Although measurement accuracy of this embodiment may be effected by liquid entering the tube 122 and the air conduit, such a connection remains a viable, albeit less robust alternative.

Still further, the pressure sensor 120 may be positioned near the distal end 126 of the resectoscope shaft 152 to directly sense fluid pressure in the body cavity B when the resectoscope is in operation. It should be understood that a pressure sensor 120 located near the distal tip 126 would be sufficiently miniaturized or otherwise configured to minimize its exposure on the external surface of the resectoscope sheath 52 or in the lumen of the sheath 52. Preferably, the lumen 58 inside the resectoscope sheath 52 will remain unobstructed so that tissue chips and other debris from the tissue resection may be withdrawn in an unimpeded manner. However, as mentioned above, it is much easier to couple the pressure sensor 120 to a conventional resectoscope when the sensor 120 is a detachable piece that is not directly integrated into the design of the resectoscope 50 of the present invention.

As discussed above, conventional fluid management systems have had difficulty controlling pump output to maintain a desired pressure within a body cavity B over varying fluid flow rates. The controlled infusion system 10 of the present invention uses a first pressure sensor 110 and a second sensor 120 which measure pressure at a first point and second point along a fluid flow path to provide a stable and responsive cavity pressure control. Additional pressure sensor(s) may be used, but usually two sensor employed as described below will be sufficient. Preferably, the first 110 sensor is located just downstream from the pump 40 so that the pump output pressure is closely monitored. The second sensor 120 measures pressure at or near the distal end of the resectoscope 52 so that the pressure inside the body cavity B can be sensed when the resectoscope is in operation. In general terms, having a pressure sensor close to the pump provides faster, more stable control of the pump while a second sensor measuring pressure within the body cavity B permits the system to control the pump set point to the desired level to achieve the target body cavity pressure.

Referring now to FIG. 7A, a preferred embodiment of the control system 200 used with the present invention will be described. The control system 200 usually comprises a pump controller 210, a first pressure sensor 110, and a second pressure sensor 120. The first pressure sensor 110 and the pump controller 210 form a first control loop as indicated by arrow 220 while the second sensor 120 and the pump controller 210 form a second control loop as indicated by arrow 230. Both control loops 220 and 230 are used to regulate the speed of pump 40 based on pressure information $P_1$ from pressure sensor 110 and pressure information $P_2$ from pressure sensor 120.

In the preferred embodiment, the speed $S_p$ of the pump 40 may be defined by the following equation:

$$S_p = K (P_d - P_1 - \text{correction})$$

wherein $P_d$ is a desired uterine or body cavity pressure, K is a control gain constant that is user defined, and correction is a correction factor which is a function of $(P_d - P_2)$. $P_d - P_2$ may be interpreted as $\text{Err}_{pres}$ which is the error between the desired uterine or body cavity pressure and the actual uterine or body cavity pressure. As can be seen, the correction factor used to calculate the speed of the pump is preferably a function of the actual pressure within the body cavity measured by the second sensor 120. It is preferred that the second sensor 120 measure the pressure in the body cavity, rather than the pressure at the inflow tube 56, as there may be significant pressure losses on the order of 20 to 30 mm of Hg during delivery of fluid through the infusion instrument. In an exemplary embodiment, the correction factor is an integration of the error $\text{Err}_{pres}$ multiplied by a constant $K_c$ over a period of time dt:

$$\text{correction} = \int \text{Err}_{pres} K_c \, dt$$

Such a correction term will add incrementally larger correction values at a relatively slow rate to the function defining the speed of the pump until the error between the desired body cavity pressure and the actual body cavity pressure is reduced to zero. These equations may be modified, such as with different constant values, to calculate other control variables such as the electric power to apply to the pump 40 to generate the desired body cavity pressure.

The value of K and $K_c$ determine the size of overshoot and steady state error in the infusion system 10. If K is large, the system will be more oscillatory but also more responsive. If K is small, the opposite is true. In a preferred embodiment of the present system 200, K is selected to the largest value possible while keeping the system non-oscillatory. Any steady state error will be reduced by the correction factor which is slowly added into the function defining the speed of the pump. $K_c$ is selected to correct steady state errors as quickly as possible without in itself creating instability. Since errors are integrated, even small values of $K_c$ will eventually reduce the stead state errors to zero. Although the embodiment of the control system 200 uses a combination of integral and proportional control, it should be understood that the control system may be otherwise modified to incorporate a combination of proportional, derivative, or integral control. For example, the first control loop controlling the pump speed may incorporate proportional and derivative control to provide even faster pump response.

As discussed earlier, it is preferred that the control system 200 receive pressure information from a location immediately downstream from or near the pump and from another location within the body cavity or near the surgical target site. Such a configuration is desirable when the system 10 has a significantly long fluid flow path between the pump and the exit port or distal end 126 or the resectoscope. A long distance between the pump and the resectoscope creates a relatively slow responding system. In order to provide a stable yet accurate pressure controller, it is desirable that pressure be measured at a point close to the pump and at a point close to the resectoscope.

Figure 7B:
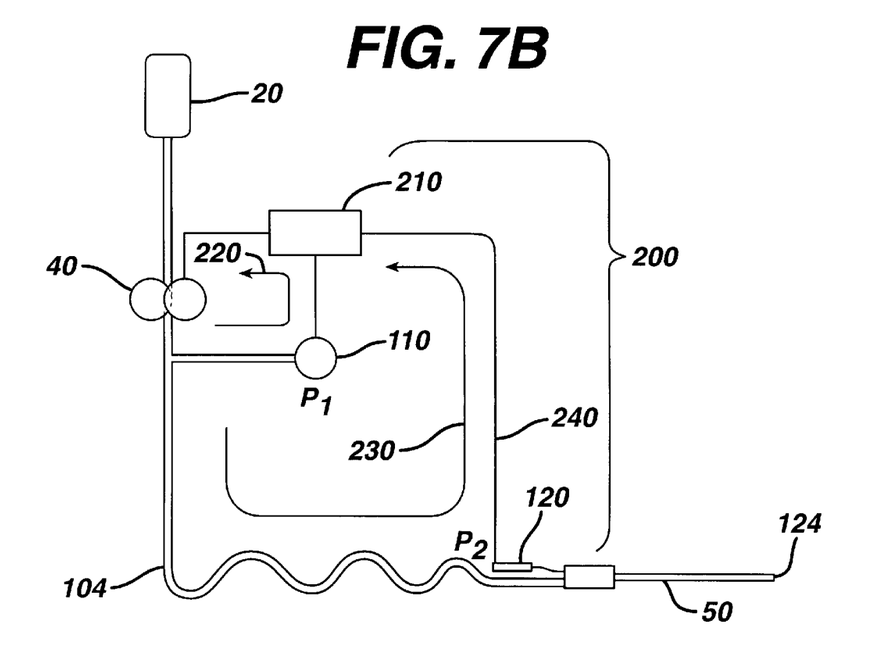
FIG. 7B is a schematic of an embodiment system according to the present invention without the bubble trap.

Referring now to FIG. 7B, the infusion system 10 of the present invention may be alternatively configured without bubble trap 100. When the trap 100 is not present, the first sensor 110 may be connected immediately downstream from the pump 40. It should be understood, however, that having bubble trap 100 provides several advantages. First, when delivering liquids through the system 10, trap 100 acts as a filter to prevent air or gas from passing from the fluid source 20 to the body cavity. Second, the bubble trap 100 acts as a flow damper where any pulsatile flow is absorbed by the body of air or gas contained in the trap 100. Third, the bubble trap 100 acts as a roll-off or low pass filter for the control system 200. This low pass filter helps the pump control 210 achieve closed loop stability and smooth pump output. The bubble trap 100 also provides a connection point for first pressure sensor 110 as shown in further detail in FIG. 2. In the preferred embodiment of the infusion system 10, the pump 40 is used to inject fluid into the bubble trap 110 which in turn pressurizes the air or gas 102. Since the trap 100 is a sealed container, except for output 104, it is actually the pressurized air or gas 102 over the fluid in the bubble trap that delivers the infusion pressure from the pump. The more air that is contained in the trap 100, the greater the damping quality of the bubble trap. Those systems that do not have a bubble trap 10 must typically incorporate some type of mathematical smoothing or damping function in their control systems.

Figure 8A:
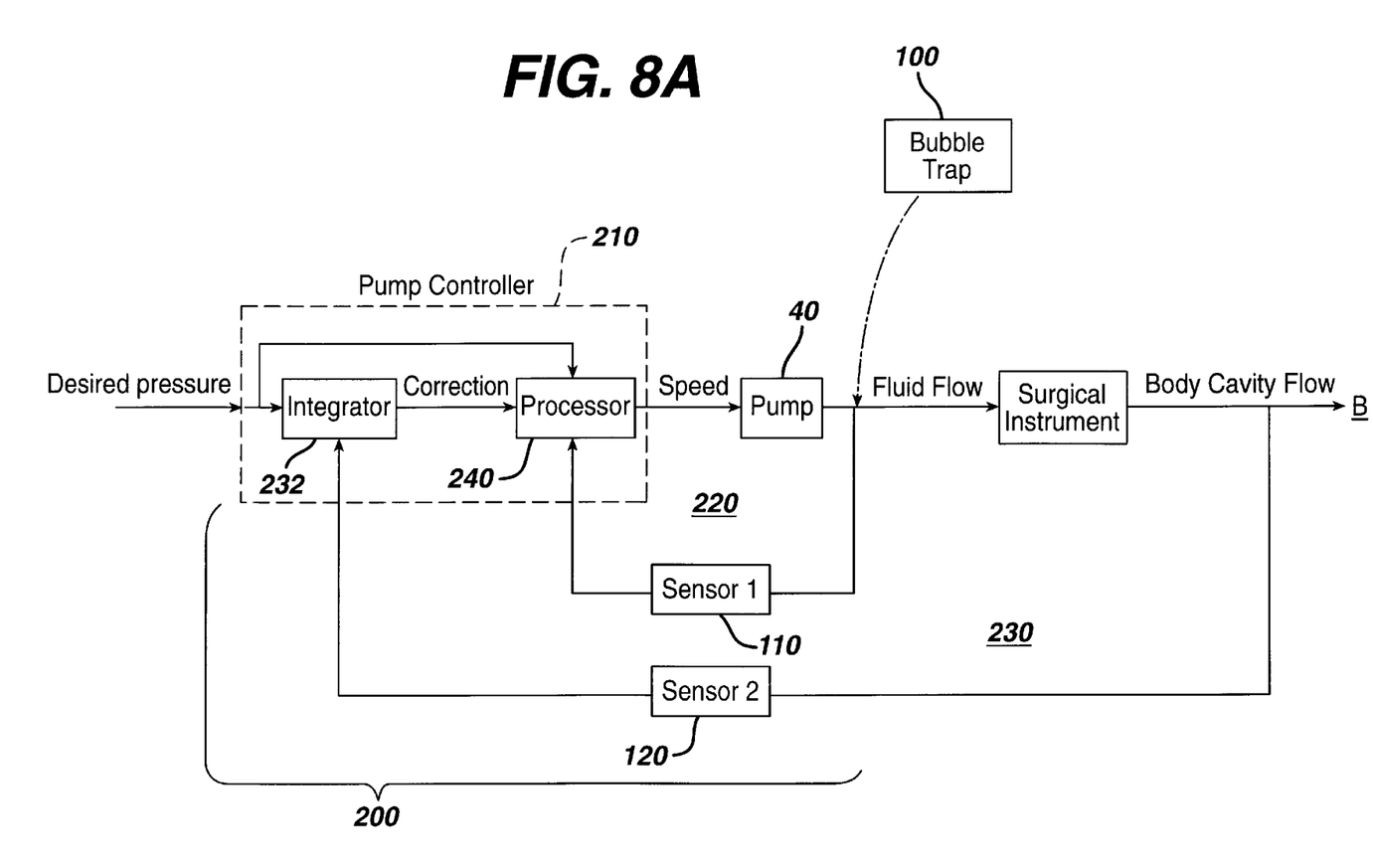
FIG. 8A is a control loop diagram of the system of FIG. 7.

Referring now to FIG. 8A, a schematic of the control system 200 will now be described. As can be seen, pump controller 210 receives a user inputted desired body cavity pressure which is passed to the integrator 232 and to the processor 240. The processor 240 uses the pressure measured by first sensor 110 to calculate a control variable such as pump speed, power to the pump, or output pressure for the pump 40. The fluid flow from the pump 40 passes into the infusion instrument 50 and then into the body cavity B. Sensor 120 measures the pressure resulting from fluid flow into body cavity B. Integrator 232 uses the desired pressure and the actual pressure within the body cavity to create a correction term which is added to the processor 240 during the next loop. As can be seen from FIG. 8A, loop 220 and loop 230 may be characterized as nested control loops. A bubble trap 100 may be included in the system to provide a roll-off point for high-frequency disturbances in the system.

Figure 8B:
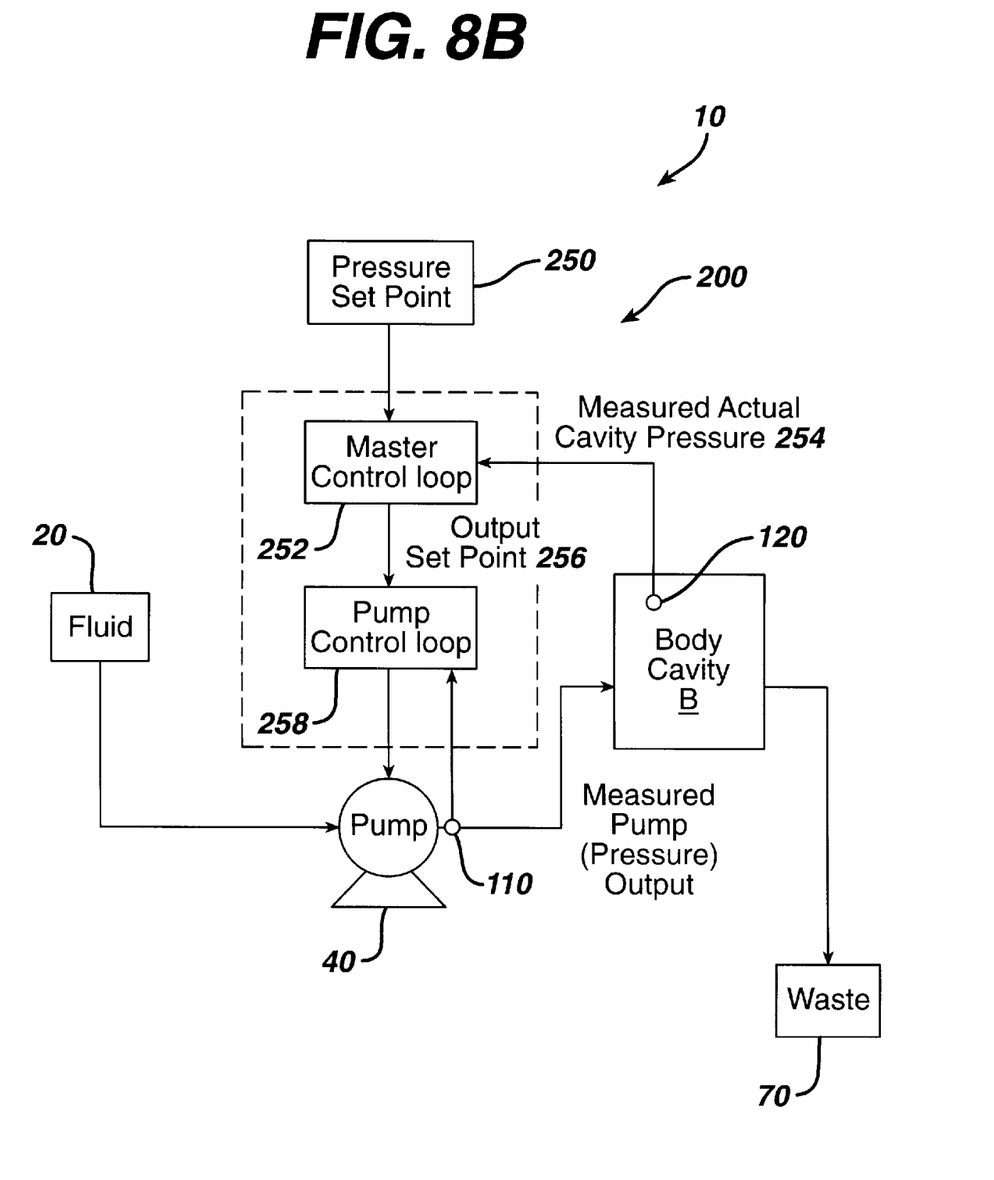
FIG. 8B is another schematic of the system of the present invention.

Alternatively, the system 200 may be embodied in the manner shown in FIG. 8B. The figure is a block diagram of a cascade control system where an output factor or variables of one control loop is passed to another control loop that regulates pump output. FIG. 8B shows that a user inputs a desired body cavity pressure, and this becomes pressure set point 250. A master control loop 252 determines a pump output set point 256 based on the pressure set point 250 and the measured actual body cavity pressure 254. The pump output set point 256 is passed onto the next control loop 258 which determines a pump control variable, such as the speed of pump 40. The pump output set point 256 is preferably a desired absolute value of pressure or possibly flow rate of the pump output. It should be understood that the pump output set point 256 may also be a correction factor of the type as described above.

Pump control loop 258 then controls pump 40 based on pump output set point 256 from loop 252. The control loop 258 preferably has a feedback configuration based on the measured pump output. As shown in FIG. 8B, the pump control loop 258 receives body cavity information from sensor 110 while master control loop 252 receives pump output information from sensor 120. Advantageously, this cascade control configuration allows for both accurate pressure control in the body cavity and improved system responsiveness. It should be understood that the pump 40 used with system 200 may be alternatively defined as having a fixed output with a variable or adjustable bypass. This provides a further method to adjust liquid pressure/flow reaching the body cavity when using a fixed output pump.

Figure 9:
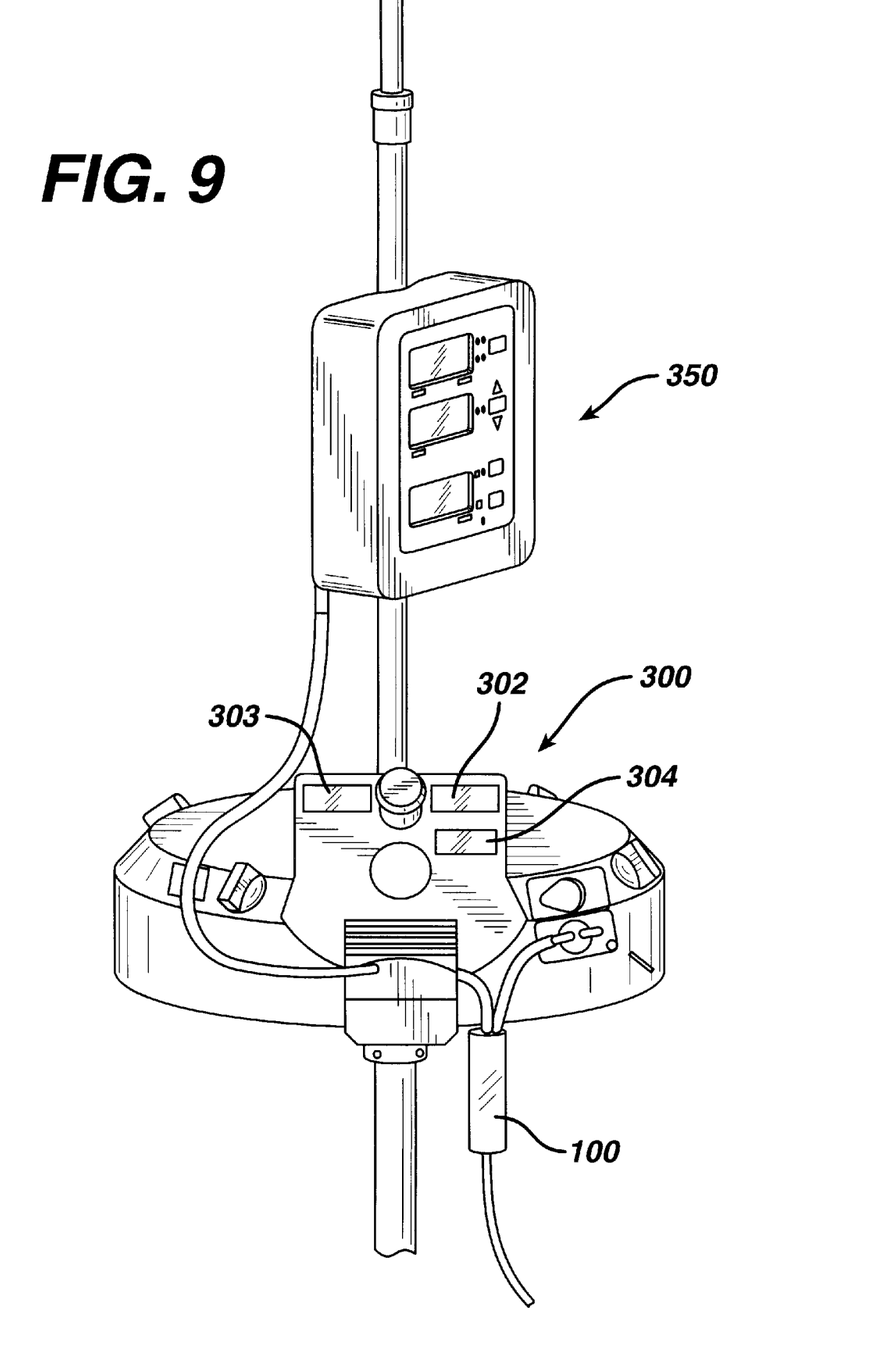
FIG. 9 shows a perspective view of one embodiment of a user interface and flow monitoring equipment for use with the present invention.

Referring now to FIG. 9, the user interface 300 of the pump 40 will now be described. The user interface 300 preferably has several large displays which are easily visible at distances of about 8 to 12 feet from the interface. The displays 302, 303, and 304 will provide information about current flow rate and current pressure and the desired pressure in the body cavity. Controllers such as knobs and buttons will be provided to activate the infusion system 10 and to select the desired flow rate and body cavity pressure of the system 10. Preferably the controls will be activatable using a gloved hand without causing discomfort or damaging the surgical gloves. Typically, the user interface 300 is integrated with the pump 40 and attached to the chassis 80. The controlled infusion system 10 may also include a display panel 350 providing information on such variables as total fluid volume delivered, and other such information. A suitable display panel 350 is described in further detail in commonly assigned, co-pending U.S. patent application Ser. No. 08/548,315, filed Nov. 1, 1995 (Attorney Docket No. 16944-000700), the full disclosure of which is incorporated herein by reference.

Although the foregoing invention has been described in some detail by way of illustration and example, for purposes of clarity of understanding, it will be obvious that certain changes and modifications may be practiced within the scope of the appended claims. For example, the infusion system may be adapted for use in transurethral resection or various arthroscopic procedures. Additionally, the sensing tube may be a stand alone device that is not directly connected to a surgical instrument such as a resectoscope or mounted on another instrument exposed to the body cavity.

What is claimed is:

1. A system for infusing fluid into a body cavity, said system comprising:

a pump having an inlet connectable to a fluid source and an outlet;

a conduit having a proximal end connectable to the pump outlet and a distal end connectable to an infusion instrument;

first sensor disposed to measure pump output pressure;

a second sensor adapted to measure body cavity pressure; and a controller defining 1) a first control loop which controls pump output based on a set point and the measured pump output and 2) a second control loop which generates the pump output set point based on a body cavity pressure set point and the measured body cavity pressure.

2. A system as in claim 1 wherein the second sensor is located near said infusion instrument.

3. A system as in claim 1 wherein the second sensor is located inside the body cavity when the system is in use.

4. A system as in claim 1 wherein the first sensor is disposed near the pump outlet.

5. A system as in claim 1 wherein said first and second control loops define a nested control loop.

6. A system as in claim 1 further comprising a bubble trap coupled to said conduit.

7. A system as in claim 6 wherein said first pressure sensor is fluidly coupled to the bubble trap.

8. A system as in claim 1 further comprising a liquid flow smoothing device.

9. A system as in claim 1 wherein said pump is a positive displacement pump.

10. A system as in claim 1 wherein said infusion instrument is a resectoscope.

11. A system as in claim I wherein the second sensor is fluidly coupled to a sensing tube coupled to a resectoscope, said tube having a static pressure port.

12. A system as in claim 11 wherein the static pressure port is located within said body cavity when the resectoscope is in use.

13. A system as in claim 1 further comprising a suction pump fluidly coupled to a fluid outlet of the infusion instrument.

14. A system for controlled infusion of fluid into a body cavity, the system comprising:

a pump having an inlet and an outlet;

a conduit defining a fluid flow path from the pump outlet;

a first sensor measuring pressure near the outlet of the pump along said fluid flow path;

a second sensor measuring pressure within the body cavity; and a pump controller adapted to control pump output based on both pressure within the body cavity and pressure near the pump.

15. A system of claim 14 wherein the pump controller is adapted to calculate pump speed as a function of a desired pressure in the body cavity, a pressure near the pump measured by a first sensor, and a correction factor.

16. A system of claim 14 wherein the pump controller is adapted to regulate pump output using a steady state error correction factor that accounts for pressure losses during fluid delivery, said correction factor being a function of the pressure near a target site in the body cavity measured by a second sensor.

17. A device for use in a body cavity comprising:

a resectoscope having a sheath; and a pressure sensor coupled to a sensing tube in said sheath, said tube having a static pressure port fluidly coupled to the body cavity.

18. A device of claim 17 wherein the resectoscope is fluidly coupled to a fluid source.

19. A device of claim 17 further comprising a cutting device located on a distal end of said sheath.

20. A method for irrigating a body cavity, said method comprising:

pumping a fluid to the body cavity using a controllable pump;

measuring pressure in the body cavity over time;

measuring pump output over time; and controlling pressure in the body cavity by (a) determining a pump output factor based on the measured body cavity pressure and (b) controlling pump output based on the pump output factor and the measured pump output.

21. A method of claim 20 wherein the pump output factor comprises a pump output pressure.

22. A method of claim 20 wherein the output value comprises a correction factor to a pump output pressure.

23. A method of claim 20 wherein pump output measuring step comprises measuring liquid pressure near the pump.

24. A method of claim 20 wherein the measuring pressure step comprises measuring liquid pressure near a target site in the body cavity.

25. A method of claim 20 wherein the changing step comprises measuring liquid pressure near a distal end of the fluid conduit.

26. A method for irrigating a body cavity comprising:

flowing fluid through a fluid conduit into the body cavity by using a pump;

sensing fluid pressure within the body cavity with a sensor located within the body cavity;

determining a correction factor based on the fluid pressure in the body cavity; and controlling pump speed based on the correction factor and fluid pressure near the pump.

27. A method of claim 26 further comprising measuring fluid pressure near a target site in the body cavity.

28. A method of claim 26 wherein controlling step comprises controlling power to the pump to control the pump speed.

29. A method of claim 26 further comprising measuring pressure from at least two locations along said fluid conduit.

30. A system for infusing fluid into a body cavity, said system comprising:

a pump having an inlet connectable to a fluid source and an outlet;

a conduit having a proximal end connectable to the pump outlet and a distal end connectable to an infusion instrument;

a first sensor disposed to measure pump output;

a second sensor located in the body cavity and adapted to measure body cavity pressure; and a controller defining 1) a first control loop which controls pump output based on a set point and the measured pump output and 2) a second control loop which generates the pump output set point based on a body cavity pressure set point and the measured body cavity pressure.

31. A system as in claim 30 wherein the first sensor is disposed to measure pump output pressure.

32. A system as in claim 30 wherein the first sensor is disposed to measure pump output flow rate.

33. A method for irrigating a body cavity comprising:

flowing fluid through a fluid conduit into the body cavity by using a pump;

measuring pressure from at least two locations along said fluid conduit;

determining a correction factor based on a fluid pressure near a target site in the body cavity; and controlling pump speed based on the correction factor and fluid pressure near the pump.

* * * * *